(12) United States Patent
Freppon

(10) Patent No.: US 6,407,320 B1
(45) Date of Patent: Jun. 18, 2002

(54) INBRED CORN LINE FR2108

(75) Inventor: Jeffrey Thomas Freppon, Deforest, WI (US)

(73) Assignee: Illinois Foundation Seeds, Inc., Champaign, IL (US)

( * ) Notice: Subject to any disclaimer, the term of this patent is extended or adjusted under 35 U.S.C. 154(b) by 0 days.

(21) Appl. No.: 09/544,989

(22) Filed: Apr. 7, 2000

(51) Int. Cl.[7] .............................. A01H 1/00; A01H 4/00; A01H 5/00; A01H 5/10; C12N 5/04
(52) U.S. Cl. ..................... 800/320.1; 435/412; 435/424; 435/430.1; 800/266; 800/268; 800/275
(58) Field of Search ............................... 800/320.1, 298, 800/275, 266, 268; 435/412, 424, 430, 430.1

(56) References Cited

PUBLICATIONS

Principles of Plant Breeding, p. 156.*
Phillips et al, Cell/Tissue Culture and In Vitro Manipulation, p. 358, section 5–2.*

\* cited by examiner

*Primary Examiner*—Amy J. Nelson
*Assistant Examiner*—Ashwin Mehta
(74) *Attorney, Agent, or Firm*—Rothwell, Figg, Ernst & Manbeck

(57) ABSTRACT

An inbred corn line, designated FR2108, is disclosed. The invention relates to the seeds of inbred corn line FR2108, to the plants of inbred corn line FR2108 and to methods for producing a corn plant produced by crossing the inbred line FR2108 with itself or another corn line. The invention further relates to hybrid corn seeds and plants produced by crossing the inbred line FR2108 with another corn line.

13 Claims, No Drawings

INBRED CORN LINE FR2108

BACKGROUND OF THE INVENTION

The present invention relates to a new and distinctive corn inbred line, designated FR2108. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, resistance to diseases and insects, better stalks and roots, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three years at least. The best lines are candidates for new commercial cultivars; those still deficient in a few traits are used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior corn inbred lines and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same corn traits.

Each year, the plant breeder selects the germplasm to advance to the next generation. This germplasm is grown under unique and different geographical, climatic and soil conditions, and further selections are then made, during and at the end of the growing season. The inbred lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop a superior new corn inbred line.

The development of commercial corn hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes. The new inbreds are crossed with other inbred lines and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., Allard, 1960; Simmonds, 1979;Sneep et al., 1979;Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the inbreds that give the best hybrid performance have been identified, the hybrid seed can be reproduced indefinitely as long as the homogeneity of the inbred parent is maintained. A single-cross hybrid is produced when two inbred lines are crossed to produce the $F_1$. progeny. A double-cross hybrid is produced from four inbred lines crossed in pairs (A×B and C×D) and then the two $F_1$, hybrids are crossed again (A×B)×(C×D). Much of the hybrid vigor exhibited by $F_1$ hybrids is lost in the next generation ($F_2$). Consequently, seed from hybrid varieties is not used for planting stock.

Corn is an important and valuable field crop. Thus, a continuing goal of plant breeders is to develop stable, high yielding corn hybrids that are agronomically sound. The reasons for this goal are obviously to maximize the amount of grain produced on the land used and to supply food for both animals and humans. To accomplish this goal, the corn breeder must select and develop corn plants that have the traits that result in superior parental lines for producing hybrids.

SUMMARY OF THE INVENTION

According to the invention, there is provided a novel inbred corn line, designated FR2108. This invention thus relates to the seeds of inbred corn line FR2108, to the plants of inbred corn line FR2108 and to methods for producing a corn plant produced by crossing the inbred line FR2108 with itself or another corn line. This invention further relates to hybrid corn seeds and plants produced by crossing the inbred line FR2108 with another corn line.

The inbred corn plant of the invention may further comprise, or have, a cytoplasmic factor that is capable of conferring male sterility. Parts of the corn plant of the present invention are also provided, such as e.g., pollen obtained from an inbred plant and an ovule of the inbred plant.

In one aspect, the present invention provides for single gene converted plants of FR2108. The single transferred gene may preferably be a dominant or recessive allele. Preferably, the single transferred gene will confer such traits as male sterility, herbicide resistance, insect resistance, resistance for bacterial, fungal, or viral disease, male fertility, enhanced nutritional quality, and industrial usage. The single gene may be a naturally occurring maize gene or a transgene introduced through genetic engineering techniques.

In another aspect, the present invention provides regenerable cells for use in tissue culture or inbred corn plant FR2108. The tissue culture will preferably be capable of regenerating plants having the physiological and morphological characteristics of the foregoing inbred corn plant, and of regenerating plants having substantially the same genotype as the foregoing inbred corn plant. Preferably, the regenerable cells in such tissue cultures will be embryos, protoplasts, meristematic cells, callus, pollen, leaves, anthers, roots, root tips, silk, flowers, kernels, ears, cobs, husks or stalks. Still further, the present invention provides corn plants regenerated from the tissue cultures of the invention.

DEFINITIONS

In the description and tables which follow, a number of terms are used. In order to provide a clear and consistent understanding of the specification and claims, including the scope to be given such terms, the following definitions are provided:

Predicted RM. This trait for a hybrid, predicted relative maturity (RM), is based on the harvest moisture of the grain. The relative maturity rating is based on a known set of checks and utilizes conventional maturity systems such as the Minnesota Relative Maturity Rating System.

MN RM. This represents the Minnesota Relative Maturity Rating (MN RM) for the hybrid and is based on the harvest moisture of the grain relative to a standard set of checks of previously determined MN RM rating. Regression analysis is used to compute this rating.

Yield (Bushels/Acre). The yield in bushels/acre is the actual yield of the grain at harvest adjusted to 15.5% moisture.

Moisture. The moisture is the actual percentage moisture of the grain at harvest.

GDU Silk. The GDU silk (=heat unit silk) is the number of growing degree units (GDU) or heat units required for an inbred line or hybrid to reach silk emergence from the time of planting. Growing degree units are calculated by the Barger Method, where the heat units for a 24-hour period are:

$$GDU = \frac{(Max.+Min)}{2} - 50.$$

The highest maximum used is 86° F. and the lowest minimum used is 50° F. For each hybrid, it takes a certain number of GDUs to reach various stages of plant development. GDUs are a way of measuring plant maturity.

Stalk Lodging. This is the percentage of plants that stalk lodge, i.e., stalk breakage, as measured by either natural lodging or pushing the stalks determining the percentage of plants that break off below the ear. This is a relative rating of a hybrid to other hybrids for standability.

Root Lodging. The root lodging is the percentage of plants that root lodge; i.e., those that lean from the vertical axis at an approximate 30° angle or greater would be counted as root lodged.

Plant Height. This is a measure of the height of the hybrid from the ground to the tip of the tassel, and is measured in inches.

Ear Height. The ear height is a measure from the ground to the ear node attachment, and is measured in inches.

Dropped Ears. This is a measure of the number of dropped ears per plot, and represents the percentage of plants that dropped an ear prior to harvest.

Allele. The allele is any of one or more alternative forms of a gene, all of which alleles relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotypes of the $F_1$ hybrid.

Essentially all the physiological and morphological characteristics. A plant having essentially all the physiological and morphological characteristics means a plant having the physiological and morphological characteristics, except for the characteristics derived from the converted gene.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Single Gene Converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

DETAILED DESCRIPTION OF THE INVENTION

Inbred corn line FR2108 is a yellow dent corn with superior characteristics, and provides an excellent parental line in crosses for producing first generation ($F_1$.) hybrid corn.

FR2108 was developed from a broad based early flowering Ohio 43 Synthetic utilizing pedigree breeding through ear to row advancement of selected selfed plants. Rigorous selection was placed on advanced progeny for favorable plant health and agronomic characteristics. Hybrid evaluation of selected lines crossed to elite pollinators were conducted over multiple years and environments within years. Yield, stalk quality, root quality, disease tolerance, late plant greenness, late plant intactness, ear retention, pollen shedding ability, silking ability and insect tolerance were the criteria used to determine the rows from which ears were selected.

Inbred corn line FR2108 has the following morphologic and other characteristics (based primarily on data collected at Champaign, Ill. and/or Arcanum, Ohio).

VARIETY DESCRIPTION INFORMATION

1. TYPE: Dent
2. MATURITY:
   From emergence to 50% of plants in silk: 65 Days
   From emergence to 50% of plants in pollen 64 Days
3. PLANT:
   Plant Height (ground to where top leaf is attached to plant): 64 inches
   Ear Height (to base of top ear): 25 inches
4. LEAF:
   Leaf Erectness: Semi-erect
5. TASSEL:
   Anther Color: Tan
   Glume Color: Tan
6. EAR:
   Ear Length: 6 inches
   Number of Kernel Rows: 12
   Endosperm Color: Yellow
7. COB:
   Cob Color: White This invention is also directed to methods for producing a corn plant by crossing a first parent corn plant with a second parent corn plant, wherein the first or second corn plant is the inbred corn plant from the line FR2108. Further, both first and second parent corn plants may be from the inbred line FR2108. Therefore, any methods using the inbred corn line FR2108 are part of this invention: selfing, backcrosses, hybrid breeding, and crosses to populations. Any plants produced using inbred corn line FR2108 as a parent are within the scope of this invention. Advantageously, the inbred corn line is used in crosses with other corn varieties to produce first generation ($F_1$.) corn hybrid seed and plants with superior characteristics.

As used herein, the term "plant" includes plant cells, plant protoplasts, plant cell of tissue culture from which corn plants can be regenerated, plant calli, plant clumps, and plant cells that are intact in plants or parts of plants, such as pollen, flowers, kernels, ears, cobs, leaves, husks, stalks, and the like.

The present invention contemplates a corn plant regenerated from a tissue culture of an inbred (e.g., FR2108) or hybrid plant of the present invention. As is well known in the art, tissue culture of corn can be used for the in vitro regeneration of a corn plant. By way of example, a process of tissue culturing and regeneration of corn is described in European Patent Application, publication 160,390, the disclosure of which is incorporated by reference. Corn tissue culture procedures are also described in Green & Rhodes (1982) and Duncan, et al., (1985). The study by Duncan et al., (1985) indicates that 97 percent of cultured plants produced calli capable of regenerating plants. Subsequent studies have shown that both inbreds and hybrids produced 91 percent regenerable calli that produced plants.

Other studies indicate that non-traditional tissues are capable of producing somatic embryogenesis and plant regeneration. See, e.g., Songstad et al., (1988); Rao et al., (1986); and Conger et al., (1987), the disclosures of which are incorporated herein by reference. Regenerable cultures may be initiated from immature embryos as described in PCT publication WO 95/06128, the disclosure of which is incorporated herein by reference.

Thus, another aspect of this invention is to provide for cells which upon growth and differentiation produce the inbred line FR2108.

When FR2108 is compared to FR448, an inbred of similar maturity and usage, FR2108 has higher yield and test weight but lower grain harvest moisture than FR448. FR2108 is a short inbred with low ear placement and flowers similar to FR448. The two inbreds have similar seedling vigor but FR2108 has a higher early stand count. FR2108 has better stay green and is more resistant to stalk lodging and root lodging than FR448. FR2108 is more resistant to Northern Corn Leaf Blight and first and second generation corn borer and more resistant to common rust than FR448.

When FR2108 is compared to FR9661, an inbred of similar maturity and usage, FR2108 has lower yield, test weight, and lower grain harvest moisture than FR9661. FR2108 is significantly shorter with lower ear placement and flowers a day or two days later when compared to FR9661. FR2108 has lower seedling vigor and lower early stand count when compared to FR9661. FR2108 has less pollen weight and smaller tassel compared to FR9661. FR2108 has poorer stay green and is more susceptible to stalk lodging than FR9661. FR2108 has less resistance to common rust, Northern Corn Leaf Blight, Stewart's wilt and first brood European corn borer, ear mold, and Southern Corn Leaf Blight compared to FR9661.

Some of the criteria used to select ears in various generations include: yield, stalk quality, root quality, disease tolerance, late plant greenness, late season plant intactness, ear retention, pollen shedding ability, silking ability, and corn borer tolerance. During the development of the line, crosses were made to inbred testers for the purpose of estimating the line's general and specific combining ability, and evaluations were run by the Champaign, Ill. and/or Arcanum, Ohio Research Station. The inbred was evaluated further as a line and in numerous crosses by other research stations across the Corn Belt.

The inbred has proven to have a very good combining ability in hybrid combinations.

The inbred has shown uniformity and stability. It has been self-pollinated and ear-rowed a sufficient number of generations, with careful attention to uniformity of plant type to ensure homozygosity and phenotypic stability. The line has been increased both by hand and sibbed in isolated fields with continued observations for uniformity. No variant traits have been observed or are expected in FR2108.

TABLES

In the tables that follow, the traits and characteristics of inbred corn line FR2108 are given in hybrid combination. The data collected on inbred corn line FR2108 is presented for the key characteristics and traits. The tables present yield test information about FR2108. FR2108 was tested in several hybrid combinations at numerous locations, with two or three replications per location. Information about these hybrids, as compared to several check hybrids, is presented.

The first pedigree listed in the comparison group is the hybrid containing FR2108. Information for the pedigree in the tables below includes:

1. Yield (YLD) in bushels/acre is the actual yield of the grain at harvest adjusted to 15.5% moisture.
2. A mean for the percentage moisture (% M) for the hybrid across all locations at harvest.
3. A mean of the yield divided by the percentage moisture (Y/M) for the hybrid across all locations.
4. The root lodging (RL) is the percentage of plants that root lodge; i.e., those that lean from the vertical axis at an approximate 30 degree angle or greater would be counted as root lodged.
5. Stalk lodging (SL) is the percentage of the plants that stalk lodge, i.e., stalk breakage, as measured by either natural lodging or pushing the stalks determining the percentage of plants that break off below the ear. This is a relative rating of a hybrid to other hybrids for standability.
6. Ear Height (EH) is measured from the soil level to the node at which the upper ear was attached and is expressed in inches.
7. Staygreen (SG) is a subjective rating on a scale of 1 to 7 during the fall. A rating of 1 represents a plant with no dead leaf tissue and a 7 represents a plant with all leaf tissue dead. A rating of 1 is the most desirable.
8. Field Score (FS) is a subjective rating of a scale of 1 to 9 made just prior to harvest. A rating of 1 represents a hybrid with a very good plant integrity after senescence and a 9 represents a hybrid with very poor plant integrity after senescence. A rating of 1 is the most desirable.

The series of hybrids listed under the hybrid containing FR2108 are considered check hybrids. The check hybrids are compared to hybrids containing the inbred FR2108.

TABLE 1

| 1998 COMPARISONS at 11 Locations | | | | | | | | |
|---|---|---|---|---|---|---|---|---|
| Pedigree | YLD | % M | Y/M | RL | SL | EH | SG | FS |
| FR2108 x FR1064 | 207 | 19.20 | 10.90 | 6 | 3 | 44 | 3.9 | 3.4 |
| Pioneer 3730 | 185 | 19.10 | 9.80 | 10 | 4 | 38 | 4.6 | 5.1 |
| Pioneer 3753 | 177 | 18.30 | 9.70 | 15 | 6 | 41 | 5.7 | 5.4 |

TABLE 2

| 1999 COMPARISONS at 13 Locations | | | | | | | | |
|---|---|---|---|---|---|---|---|---|
| Pedigree | YLD | % M | Y/M | RL | SL | EH | SG | FS |
| FR2108 x FR1064 | 172 | 25.30 | 6.80 | 0 | 1 | 40 | 4.0 | 3.0 |
| Pioneer 36K50 | 162 | 20.80 | 7.80 | 0 | 1 | 40 | 5.0 | 4.1 |
| Pioneer 36H36 | 159 | 22.40 | 7.10 | 0 | 1 | 40 | 5.0 | 3.8 |
| Pioneer 3730 | 158 | 22.50 | 7.00 | 0 | 1 | 39 | 3.5 | 3.3 |

In both 1998 (Table 1) and 1999 (Table 2) FR2108 crossed to the inbred tester FRi 064 (102 days to relative maturity {DRM}) was higher yielding than Pioneer hybrid 3730 (99 DRM). FR1064 is a proprietary corn inbred line of Illinois Foundation Seeds, Inc. and is widely used in the U.S. corn belt. The two hybrids had similar grain moisture at harvest in 1998, but the FR2108 hybrid was wetter in 1999 than Pioneer 3730. In both years the FR2108 hybrid had a lower Y/M ratio than Pioneer 3730. In 1998 the FR2108 hybrid had better root and stalk quality than Pioneer 3730, but both hybrids had equivalent standability in 1999. The FR2108 had a more favorable staygreen and field score than Pioneer 3730 in 1998 and similar staygreen and field score in 1999.

In 1998 (Table 1), FR2108 crossed to the inbred FR1064 (102 DRM) was compared to Pioneer hybrid 3753 (96 DRM). The FR2108 hybrid was higher yielding, wetter with a lower Y/M than Pioneer 3753. The FR2108 hybrid had better root and stalk quality, and a more favorable staygreen and field score than the Pioneer 3753.

In 1999 (Table 2) FR2108 crossed to the inbred FR1064 (102 DRM) is compared to Pioneer hybrids 36K50 (101 DRM) and 36H36 (100 DRM). Compared to 36K50, the FR2108 hybrid had higher yield, wetter grain at harvest and a lower Y/M ratio. Both hybrids had equivalent standability with the FR2108 hybrid had a more favorable staygreen and field score rating than Pioneer 36K50. Compared to 36H36, the FR2108 hybrid had higher yield, wetter grain at harvest and a lower Y/M ratio. Both hybrids had equivalent standability. The FR2108 hybrid had a more favorable staygreen and field score than Pioneer 36H36.

When the term inbred corn plant is used in the context of the present invention, this also includes any single gene conversions of that inbred. The term single gene converted plant as used herein refers to those corn plants which are developed by a plant breeding technique called backcrossing wherein essentially all of the desired morphological and physiological characteristics of an inbred are recovered in addition to the single gene transferred into the inbred via the backcrossing technique. Backcrossing methods can be used with the present invention to improve or introduce a characteristic into the inbred. The term backcrossing as used herein refers to the repeated crossing of a hybrid progeny back to one of the parental corn plants for that inbred. The parental corn plant which contributes the gene for the desired characteristic is termed the nonrecurrent or donor parent. This terminology refers to the fact that the nonrecurrent parent is used one time in the backcross protocol and therefore does not recur. The parental corn plant to which the gene or genes from the nonrecurrent parent are transferred is known as the recurrent parent as it is used for several rounds in the backcrossing protocol (Poehiman & Sleper, 1994;Fehr, 1987). In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated until a corn plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original inbred. To accomplish this, a single gene of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new inbred but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212; the disclosure of which is specifically incorporated herein by reference.

A further aspect of the invention relates to tissue culture of corn plants designated FR2108. As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, kernels, ears, cobs, leaves, husks, stalks, roots, root tips, anthers, silk and the like. In a preferred embodiment, tissue culture is embryos, protoplast, meristematic cells, pollen, leaves or anthers. Means for preparing and maintaining plant tissue culture are well known in the art. By way of example, a tissue culture comprising organs such as tassels. or anthers, has been used to produce regenerated plants. (See U.S. Pat. Nos. 5,445,961; 5,322,789; 5,948,957 and 5,969,212, the disclosures of which are incorporated herein by reference).

DEPOSIT INFORMATION

A deposit of the Ill. Foundation Seeds, Inc. proprietary inbred corn line FR2108 disclosed above and recited in the appended claims has been made with the American Type Culture Collection (ATCC), 10801 University Boulevard, Manassas, Va. 20110. The date of deposit was Feb. 27, 2002. The deposit of 2,500 seeds were taken from the same deposit maintained by Ill. Foundation Seeds, Inc. since prior to the filling date of this application. All restrictions upon the deposit have been removed, and the deposit is intended to meet all of the requirements of 37 C.F.R. §1.801–1.809. The ATCC accession number is PTA-4104. The deposit will be maintained in the depository for a period of 30 years, or 5 after the last request, or for the effective life of the patent, whichever is longer, and will be replaced as necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. An inbred corn seed designated FR2108, a sample of said seed having been deposited under ATCC Accession No. PTA-4104.

2. A corn plant, or parts thereof, produced by growing the seed of claim 1.

3. Pollen of the plant of claim 2.

4. An ovule of the plant of claim 2.

5. The corn plant of claim 2, wherein said plant is male sterile.

6. A tissue culture of regenerable cells of a corn plant of inbred line FR2108, wherein the tissue regenerates plants capable of expressing all the morphological and physiological characteristics of the inbred line FR2108; a sample of said seed having been deposited under ATCC Accession No. PTA-4104.

7. A tissue culture according to claim 6, the cells or protoplasts being from a tissue selected from the group consisting of leaves, pollen, embryos, roots, root tips, anthers, silks, flowers, kernels, ears, cobs, husks, and stalks.

8. A method for producing a hybrid corn seed comprising crossing a first inbred parent corn plant with a second inbred parent corn plant and harvesting the resultant hybrid corn seed, wherein said first or second parent corn plant is the corn plant of claim 2.

9. A hybrid corn seed produced by the method of claim 8.

10. A hybrid corn plant, or, parts thereof, produced by growing said hybrid corn seed of claim 9.

11. Corn seed produced by growing said hybrid corn plant of claim 10.

12. A corn plant, or parts thereof, produced from seed of claim 11.

13. A method for producing a hybrid corn seed comprising crossing an inbred plant according to claim 2 with another, different corn plant.

* * * * *